(12) United States Patent
Kwong

(10) Patent No.: US 6,917,829 B2
(45) Date of Patent: Jul. 12, 2005

(54) METHOD AND SYSTEM FOR A DISTRIBUTED ANALYTICAL AND DIAGNOSTIC SOFTWARE OVER THE INTRANET AND INTERNET ENVIRONMENT

(75) Inventor: Manlik Kwong, Corvallis, OR (US)

(73) Assignee: Clinical Care Systems, Inc., Wellesley, MA (US)

( * ) Notice: Subject to any disclaimer, the term of this patent is extended or adjusted under 35 U.S.C. 154(b) by 377 days.

(21) Appl. No.: 09/925,612

(22) Filed: Aug. 9, 2001

(65) Prior Publication Data

US 2002/0107452 A1 Aug. 8, 2002

Related U.S. Application Data

(60) Provisional application No. 60/224,052, filed on Aug. 9, 2000.

(51) Int. Cl.[7] ............................................. A61B 5/0402
(52) U.S. Cl. ....................................................... 600/509
(58) Field of Search ................................ 600/509, 513, 600/515, 300, 301; 128/920, 923–925

(56) References Cited

U.S. PATENT DOCUMENTS

| 5,724,025 A | 3/1998 | Tavori ......................... 340/573 |
| 6,067,466 A | 5/2000 | Selker et al. | |

FOREIGN PATENT DOCUMENTS

| WO | 00/30529 | 6/2000 |

Primary Examiner—Jeffrey R. Jastrzab
(74) Attorney, Agent, or Firm—Wilmer Cutler Pickering Hale and Dorr LLP

(57) ABSTRACT

An apparatus for monitoring the medical condition of a patient, including a monitoring device which during use monitors one or more clinical features of the patient; a predictive instrument arranged to receive output from the monitoring device and programmed to compute a probability of a medical outcome or diagnosis based on the monitored one or more clinical features, the predictive instrument further programmed to compute that probability by executing an algorithm which models the medical outcome or diagnosis; and an interface through which a user enters information characterizing the patient, wherein the predictive instrument is further programmed to request that algorithm from a remote location.

21 Claims, 6 Drawing Sheets

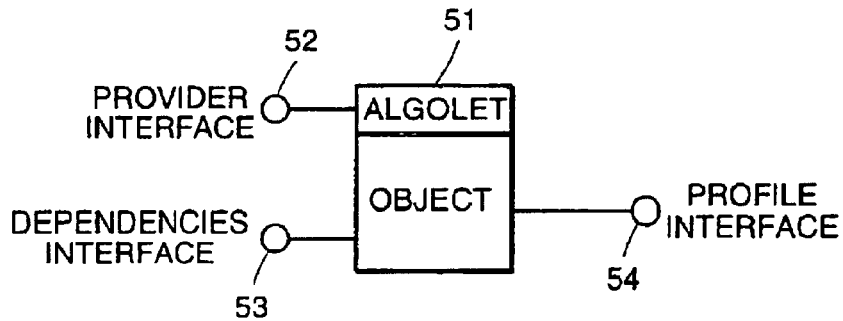
FIG. 5.1
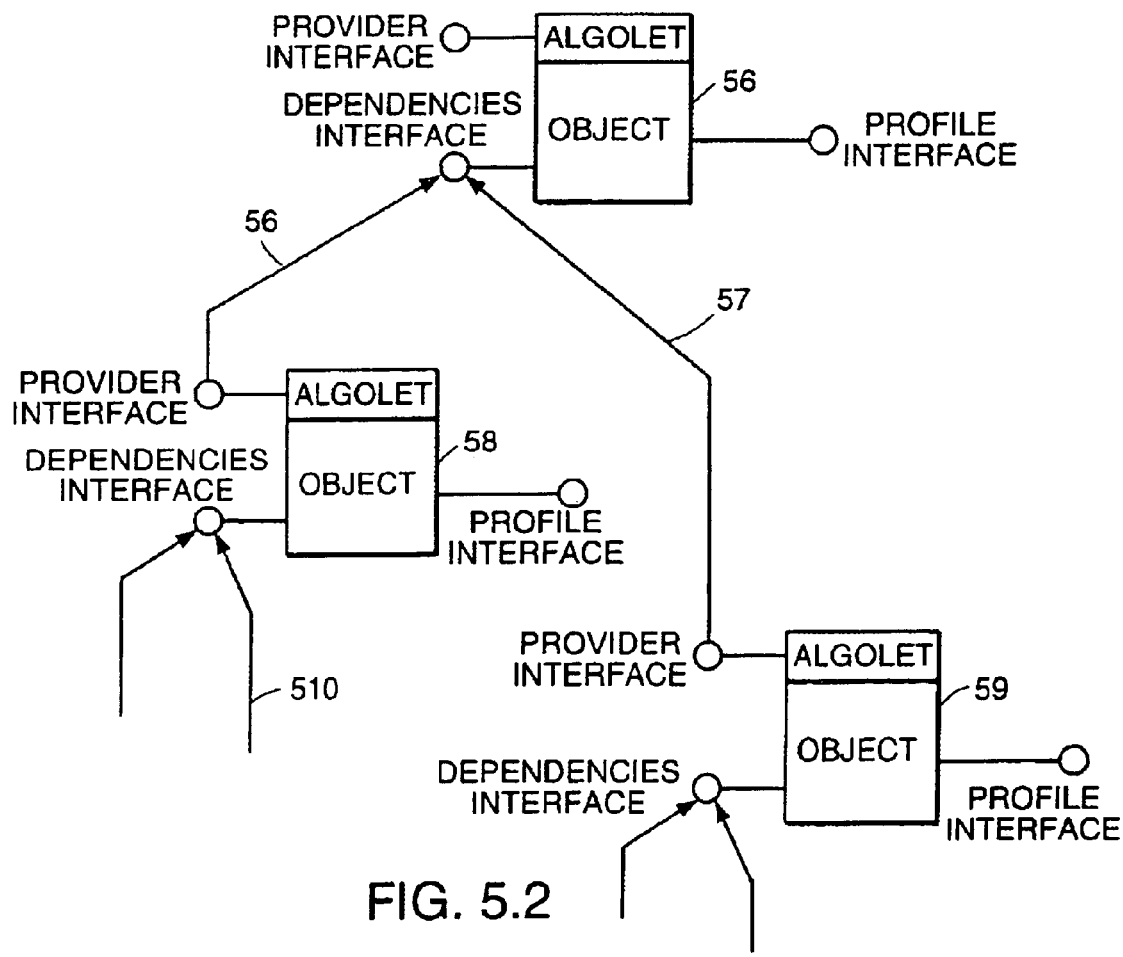
FIG. 5.2

METHOD AND SYSTEM FOR A DISTRIBUTED ANALYTICAL AND DIAGNOSTIC SOFTWARE OVER THE INTRANET AND INTERNET ENVIRONMENT

CROSS REFERENCE TO RELATED APPLICATION

This application claims the benefit of U.S. provisional application Ser. No. 60/224,052, filed Aug. 9, 2000.

BACKGROUND OF THE INVENTION

The present invention relates, in general, to programmable medical instruments for computing probabilities of medical outcomes or diagnoses.

A number of instruments have been developed that enable the physician to compute probabilities of life threatening cardiac conditions for patients. Some of these instruments are described in the following references, all of which are incorporated herein be reference.

A hand-held predictive instrument is described by Michael W. Pozen et al. in "A Predictive Instrument to Improve Coronary-Care- Unit Admission Practices in Acute Ischemic Heart Disease" The New England Journal of Medicine, Vol 310 pp. 1273–1278, May 17, 1984. With the handheld calculator-based instrument, a physician can compute a patient's probability of having acute cardiac ischemia based upon physician-entered values for a set of clinical variables. An automatic, computerized version of this instrument which utilizes output from a electrocardiograph and a waveform analyzer is described by H. P. Selker et al. in "A Time-Insensitive Predictive Instrument for Acute Myocardial Infarction Mortality", Med. Care 1991; 29:1196–1211.

A predictive instrument for determining the probability of acute hospital mortality of a cardiac patient is described in U.S. Pat. No. 4,957,115 to Dr. Harry P. Selker, and incorporated herein by reference. The probability of acute hospital mortality is commonly understood to mean the probability of dying from a current acute condition, generally during the specific initial hospitalization for the problem. It is also know as the probability of imminent death for the patient. That is, it is a short term, as opposed to a long term, probability of mortality that does not necessarily have a precisely defined period of time associated with it.

A predictive instrument for evaluating whether to use thrombolytic therapy to treat a patient with a heart condition is described in U.S. Pat. No. 4,998,535 to Dr. Selker et al., and incorporated herein by reference. The predictive instrument computes a first probability of acute hospital mortality for the patient assuming that thrombolytic therapy is not administered and it computes a second probability of acute hospital mortality for the patient assuming that thrombolytic therapy is administered. The difference in the computed probabilities may assist the physician in deciding whether it would be advantageous to administer the thrombolytic therapy to the patient.

The above-mentioned predictive instruments use logistic regression equations to model the probability that the patient has a serious cardiac condition (e.g. the probability of acute cardiac ischemia or the probability of imminent death from a cardiac condition). Such predictive instruments have also been suggested for other medical conditions or medical outcomes. See for example, U.S. Pat. No. 5,724,983 to Dr. Selker et al. also incorporated herein by reference.

SUMMARY OF THE INVENTION

In general, in one aspect, the invention features an apparatus for monitoring the medical condition of a patient. The apparatus includes a monitoring device which during use monitors one or more clinical features of the patient; a predictive instrument arranged to receive output from the monitoring device and programmed to compute a probability of a medical outcome or diagnosis based on the monitored one or more clinical features; and an interface through which a user enters information characterizing the patient. The predictive instrument is programmed to request an algorithm which models the medical outcome or diagnosis from a remote location and is further programmed to compute the probability by executing that algorithm.

Preferred embodiments may include one or more of the following features. The monitoring device is an electrocardiograph. The algorithm enables the predictive instrument to compute said probability using a regression equation. More specifically, the regression equation is of the form:

$$P = 100\left[1 - \frac{1}{1 + e^{b_0 + \Sigma b_i x_i}}\right]$$

where P is the probability of medical outcome or diagnosis, $b_0$ is a constant, the $x_i$'s are explanatory variables, and the $b_i$'s are coefficients of corresponding explanatory variables. Also, in some cases P is a probability of acute cardiac ischemia.

In general, in another aspect, the invention features an apparatus for enabling a remotely located predictive instrument to compute a probability of a medical outcome or diagnosis based on monitored one or more clinical features of a patient. The apparatus includes a data storage area which stores a plurality of different algorithms, each of which models a corresponding medical outcome or diagnosis; and a server which is programmed to respond to a request from a remote device by retrieving a selected one of the plurality of different algorithms from the data storage and forwarding the selected algorithm to the remote device.

In preferred embodiments, the request contains a patient profile and the server identifies which of the plurality of different algorithms is the selected algorithm based on the received patient profile.

In general, in still another aspect, the invention features a method for evaluating a medical condition of a patient. The method includes receiving input characterizing the patient; electronically retrieving from a remote location, an algorithm for computing a probability of a medical outcome or diagnosis; monitoring one or more clinical features of a patient; and using the retrieved algorithm to compute the probability of the medical outcome or diagnosis for the patient and based on the monitored features.

In one aspect, the invention features an improved method and system to distribute matched analytical and diagnostic software components to an individual patient.

In another aspect, the present invention features an improved method and system in which existing analytical and diagnostic software components can be improved upon and support the creation of new analytical and diagnostic software components for patient groups that have not been adequately addressed by prior art methods and systems.

In another aspect, the present invention features an analytical and diagnostic software component lookup service to make available existing analytical and diagnostic software components to compliant networked instruments and systems.

In general, in one aspect the invention relates to a new method and system to provide lookup and distribution of individualized medical analytical and diagnostic software components over a network, including, but not exclusively within an intranet or the Internet and, in particular, to enable appropriately equipped networked medical instruments and systems to lookup and request appropriately matched analytical and diagnostic software component(s) for improved patient management and care. In other words, the invention provides the framework in which better analytical and diagnostic software components may be created, improved, and made available to subsequent patients through their patient healthcare providers.

In general, in another aspect the invention has applicability to medical systems used to address cardiovascular diseases. Many prior art methods and systems in this area utilize analytical and diagnostic software components based on narrowly derived patient population and characteristics. In particular, many prior art methods and systems in electrocardiographic instruments and systems analysis and diagnostic are based on a fixed analytic and diagnostic software component for a general population of Caucasian middle age males and to some extent middle age Caucasian females. In the area of cardiovascular diseases, the invention provides a method and system to enable both the availability and creation of highly individualized analytical and diagnostic software component based on a patient's presenting demographics and locality. Thus, this application of the invention enables a much more appropriate application of prior medical knowledge and practices.

According to some embodiments of the invention, the method and system work by designing and implementing individual analytical and diagnostic software components according to Object Oriented practices to a pre-defined interface or application programming interface (API). An interface or API provides, in terms of computerized software, a "contract" upon the software component that implements the API to provide for a set of "methods" or functions or procedures as defined by the API. This enables the framework in which the software component is loaded to service requests by the framework or container upon the loaded software component.

Specifically, those embodiments of the present invention implement these software components as both Java Beans and Enterprise Java Beans. The framework or container in which these Java components are loaded can be network enabled applications that supports loading and executing Java Beans and Enterprise Java Beans. Of course, other components framework and technologies such as Microsoft's COM/COM+ and DCOM can also be used to implement this invention.

The method and system also provide for a repository of all available analytical and diagnostic software components. This repository supports intranet and Internet lookup services via the Java Naming and Directory Interface (JNDI) repository lookup technology. This lookup service enables compliant instruments and system to query all available analytical and diagnostic software components that best match a patient's demographic and geographic profile.

The method and system also provide for a feedback mechanism in which clinician directed diagnosis and patient outcome information can be feed back to enable the development of new and improved analytical and diagnostic software components to be placed in the analytical and diagnostic software components repository.

Therefore the present invention provides a self-improving and self-sustaining system for providing distributed analytical and diagnostic software components. The quality of the analytical and diagnostic software components will increase over time and with each patient served by this system.

In some aspects, the invention also provides dynamic medical analytical intelligence for medical instruments based on a patient's particular profile and desired analysis requirements. And it enables small and low-cost medical instruments to be produced without the need to implement a full range of analytical analysis capabilities; thus reducing the overall development and manufacture and extending the useful life cycle of the instrument. In addition, in other aspects the invention provides a framework to support components based medical analysis over a distributed network environment and it supports a distributed medical analysis through the use of a federation of development centers and service providers. Also, new and existing medical analysis components can be automatically and manually created, updated, and distributed over a networked environment.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 5.1 shows a representation of an Algolet component;

FIG. 5.2 illustrates the relationships among Algolet components; and

DETAILED DESCRIPTION OF THE PREFERRED EMBODIMENTS

Figure 1:
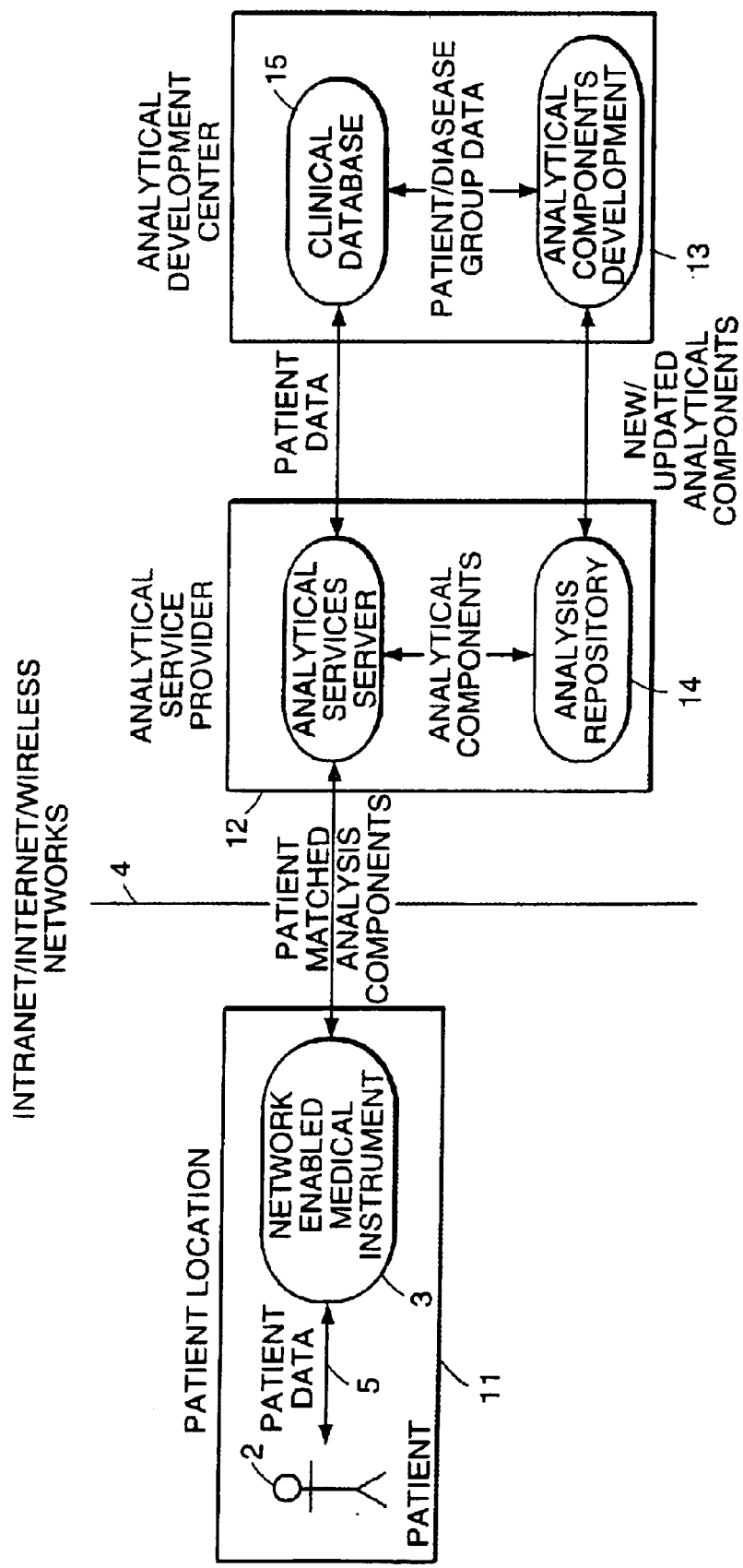
FIG. 1 is a block diagram of a system which embodies the invention.

FIG. 1 is a high level diagram of an embodiment of the invention according to which a patient 2 receives an analysis appropriate to the patient's specific characteristics or profile through the interaction of a medical instrument 3 over a network or communication connection 4 to an Analytical Service Provider system 12. The analytic services provided to medical instrument 3 can be continually improved upon; moreover, new analytical services can be created and provided for use by other compatible medical instruments.

In the embodiment shown in FIG. 1, medical instrument 3 utilizes and gains analytical intelligence first from its local algorithm repository and then from a remote algorithm repository to satisfy the needs of the particular patient with a specific patient profile. Medical instrument 3 predicts the probability of acute cardiac infarction for a given patient utilizing a network enabled electrocardiograph. Acute cardiac infarction is a condition in which the heart has lost significant blood flow, causing the onset of permanent cardiac muscle damage. The use of an electrocardiograph medical instrument is common practice in detecting and diagnosing such condition. The accuracy of identification and diagnosis of such condition is greatly dependent on many factors such as time since actual onset of the condition, patient's age, patient's gender, patient's weight, and other factors that are taken into consideration by the medical instruments shown here. In addition, the medical instrument automatically adapts its analytical capabilities to best suit a patient's immediate needs.

In the illustrated embodiment, there are three main high-level components. There is medical instrument 3 including a monitoring or measurement component, such as an electrocardiograph, connected through common means such as wired electrodes 5 to patient 2. Medical instrument 3 executes analysis of the patient's biological condition through the use of the patient's particular demographics, referred to herein as a patient's Profile, containing such information, but not limited to, age, gender, medical history, race, and other information describing the patient. Medical instrument 3 utilizes its local analytical capabilities to perform the requested analysis. If the local analytical capabilities are insufficient to provide such analysis, the medical instrument communicates over a locally connected or remotely connected network with one or more Analytical Service Providers 12. The network may be, but is not limited to, an intranet, the Internet, or a wireless network. To perform the required analysis, medical instrument 3 requests certain analytical software components, referred to herein as Algolets, from one or more available Analytical Service Providers 12.

Each Analytic Service Provider 12 utilizes the services of an Analytical Development Center 13 to provide continual automatic and manual updates to its repository 14 of analytical components (Algolets) as well as new analytical components for the identification and diagnosis of new diseases. Analytical Development Center 13 utilizes a database 15 of patient profiles, clinical presentations that might include, but are not limited to, electrocardiographic waveforms and signals, biological measurements such as chemistry, temperature, genetic information, and independently confirmed disease diagnoses by other appropriate clinical entities, such as a physician, to manually and/or automatically generate mathematical models and algorithms for identifying and diagnosing medical conditions and diseases. Each mathematical model and algorithm for example can therefore be tailored to a specific patient population or Profile such as, but not limited to, African Americans between the age of 50 and 65 with known history of hypertension.

Such mathematical models and algorithms are then packaged as an Algolet, which will be described in detail below and illustrated in FIG. 5, and delivered to the Analytic Service Provider 12.

Networked Medical Instrument

Figure 2:
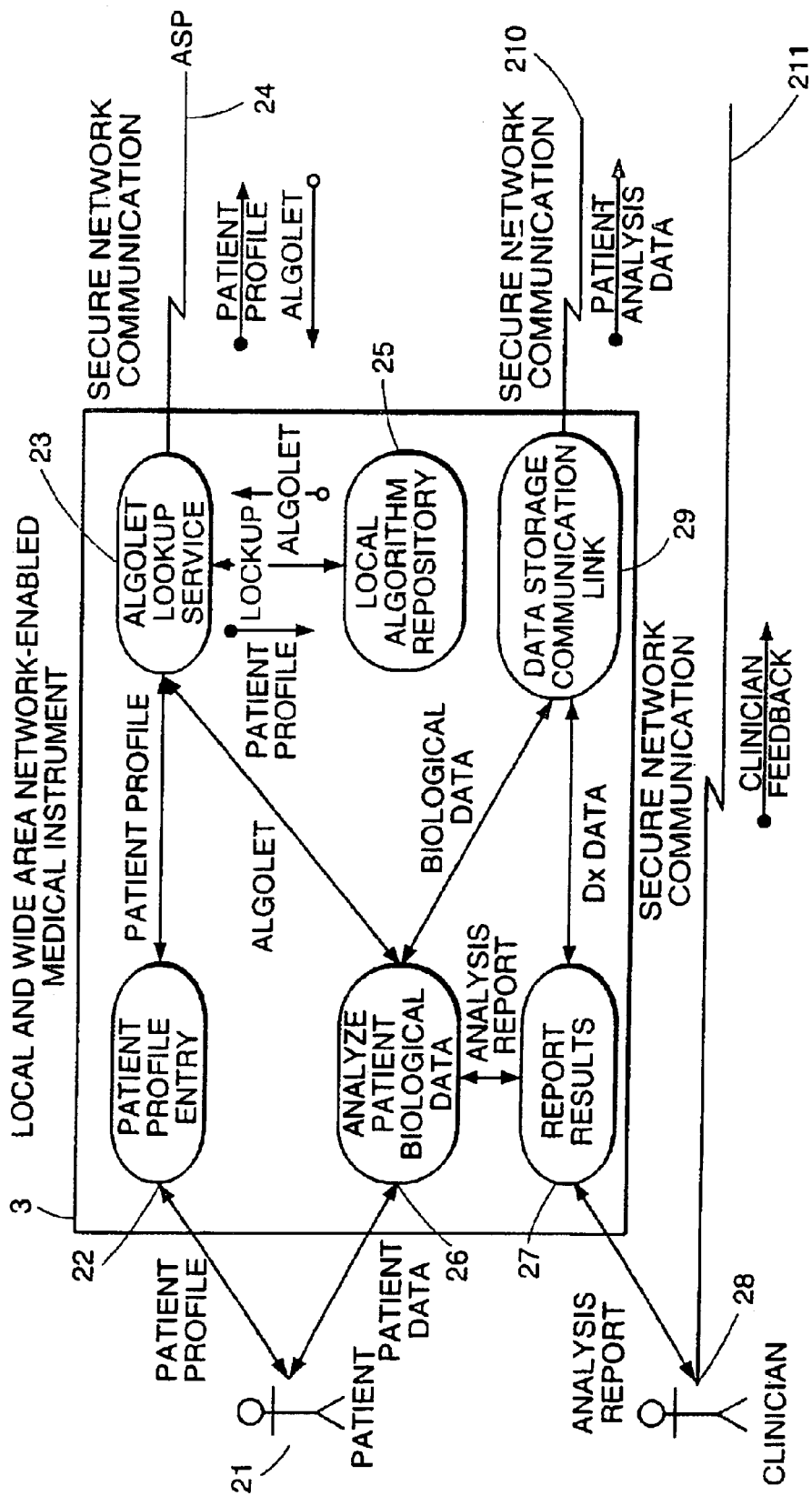
FIG. 2 shows the functionality of the Network-enabled Medical Instrument shown in FIG. 1.

FIG. 2 depicts the components of medical instrument 3 that utilizes the services provided by the Analytical Service Provider to request the best available matched analytical software algorithm components for a specific patient profile. It also depicts the feedback from a clinician 28 reviewing the reported analysis results that is used by Analytical Algorithm Development Center 13 for improving existing algorithms as well as the creation of new analysis algorithms that will be made available to Analytical Service Provider system 12.

Patient 21 requires analysis of possible acute cardiac infarction. Patient 21 enters his/her Profile data, consisting of, but not limited to, age, gender, weight, and family history using the medical instrument's Patient Profile Entry interface 22. Patient Profile entry can be done as part of pre-configuring the medical instrument. This is appropriate for patient information that does not change over relatively short periods of time and might include, but not be limited to, date of birth, race, and past medical conditions such as hypertension and diabetes. Other patient Profile information can be entered in real-time or just prior to execution of an analysis which might include, but is not limited to, heart rate, blood pressure, and temperature. A patient Profile created internally by the medical instrument is a XML record using plain ASCII text representation or as a binary Document Object Model (DOM) structure. For example, the patient Profile may appear as the following XML document:

```
<patientProfile DATE="04/06/2000 14:23:33" DATEFORMAT="M/dd/yyyy h:m:s" ID="iMedical Systems Inc.
    IMSI200">
    <demographics>
        <property ID="RACE">African American</property>
        <property ID="AGE">56</property>
        <property ID="GENDER">Male</property>
    </demographics>
    <medicalHistory>
        <medHx ID="Hypertention" DATE="0/12/1982"DATEFORMAT="M/dd/yyyy"/>treated</medHx>
    </medicalHistory>
    <vitalSigns>
        <property ID="SBP">87</property>
        <property ID="DBP">122</property>
        <property ID="TEMPERATURE" UNITS=" DEGREE">98.6</property>
        <property ID="HEARTRATE" UNITS=" BPM">94</property>
    </vitalSigns>
</patientProfile>
```

XML is a self-describing language that provides a human readable descriptive method for describing structured data such as a patient Profile. Furthermore, the internal representation of the XML-based patient Profile using the DOM construct provides adaptive and flexible representation of the same structured data. The above patient Profile example illustrates a case where the patient is a male African American of age 56 years with a past medical history of hypertension.

The patient Profile entered through interface 22 is passed to an Algolet Lookup Service 23 that will attempt to find, based on patient Profile matching, the most appropriate analysis software component that can provide the requested analysis. Lookup Service 23 first consults a Local Algorithm Repository 25. A detailed description of Algolet Lookup Service 23 is provided below and illustrated in FIG. 6. If Local Algorithm Repository 25 does not have an Algolet that can provide the requested analysis matching the patient Profile, Algolet Lookup Service 23 will connect to one or more pre-defined Analytical Service Providers over a secure network 24, such as, but not limited to, an intranet, the Internet, or wireless network to acquire the most appropriate analysis capability that best matches the patient's Profile. This ability to consult external sources for acquisition of analytical software components provides extensive flexibility and expansion capabilities without having to create a new medical instrument to host such capabilities.

Figure 3:
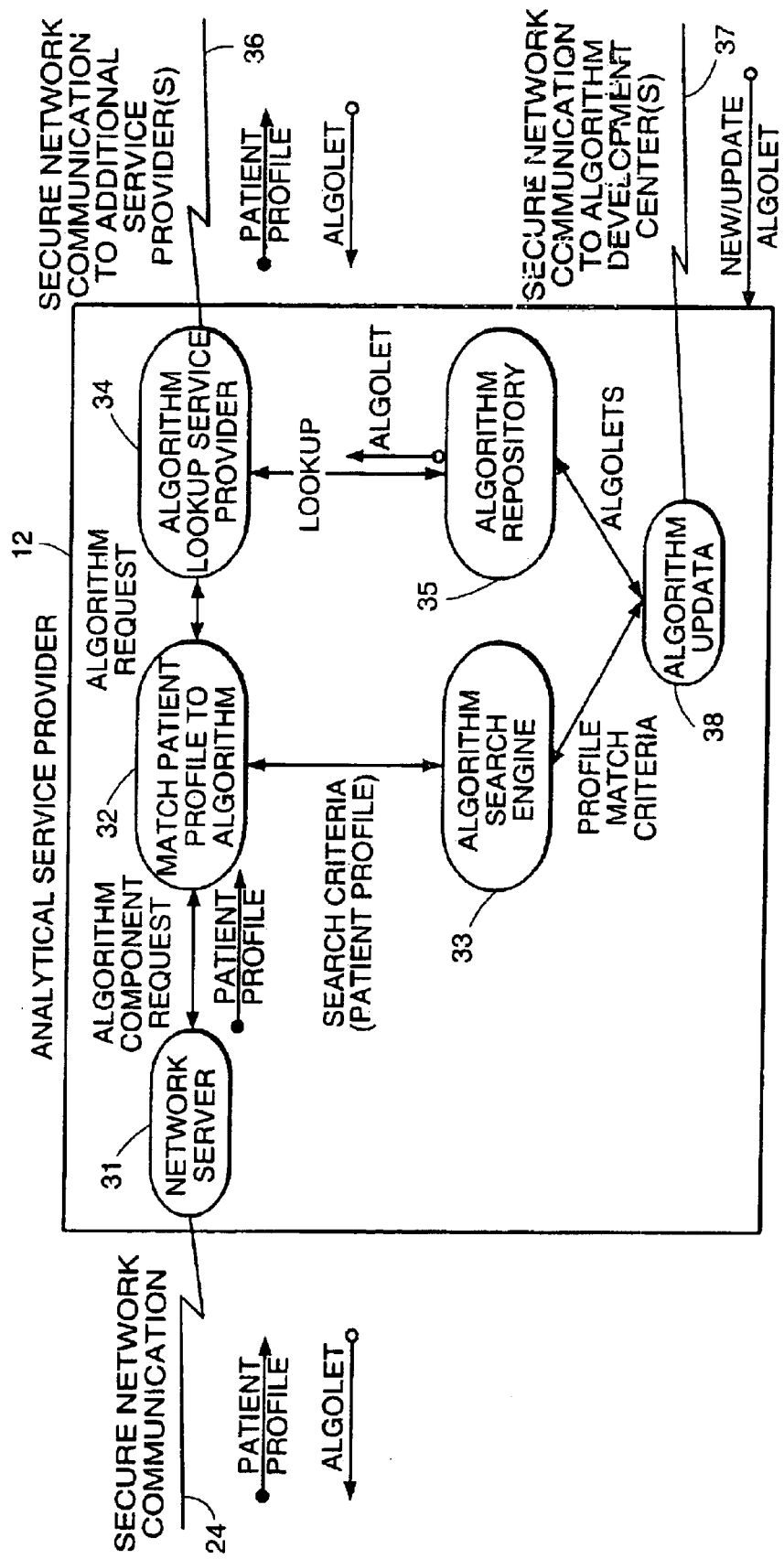
FIG. 3 shows the functionality of the Analytical Service Provider that is shown in FIG. 1.

Once the appropriate or best analysis software component(s) have been identified and downloaded over a communication link 24 from a remote Analytical Service Provider, it is first added to Local Algorithm Repository 25. Local Algorithm Repository 25 is managed by the medical instrument using various methods such as, but not limited to, memory availability, first-in-first out algorithm, or most frequently used Algolet algorithms. The analysis software component(s) is then passed onto an analysis component 26 for execution utilizing additional patient biological signals such as the cardiac electrical signal in the form of a 3-lead or 12-lead or 16-lead electrocardiogram. Once the analysis is complete, the biological data and results of the analysis are forwarded to a reporting module 27 for presentation to a clinician 28 for confirmation and review. In addition, the biological data and analysis results are also archived locally and/or forwarded via a data storage communication link 29 to a remote database storage facility such as the Analytical Algorithm Development Center (as illustrated by communication link 210). Clinician 28 or another medical professional or information system involved in the care of the patient can then forward confirmed findings and diagnosis Analytical Service Provider FIG. 3 depicts the details of Analytical Service Provider 12. More specifically, FIG. 3 depicts the components utilized to match the profile to the analytical algorithm software component, to perform the algorithm software component lookup and retrieval methods, and to implement the automated and continual algorithm software component update service from the Algorithm Development Center.

Analytical Service Provider 12 is a locally or remotely located network server and database repository. Requests from medical instruments, such as described above, arrive as secure messages over Hyper-Text Transport Protocol (HTTP) over communication link 24 and are received by a Network Server 31. Server 31 utilizes a standard secure Internet Web-Server capable of receiving and processing industry standard HTTP messages. The message arriving at Network Server 31 is an extended XML message consisting of a patient Profile document such as mentioned above and requesting the particular analysis the network connected medical instrument desires. Below is an example of the XML-based message used in the described embodiment:

```
<analysis DATE="04/08/2000 15:13:22" DATEFORMAT=" M/dd/yyyy h:m:s" ID=" iMedical Systems Inc. IMSI200"
    ID="Acute Myocardial Infarction",
    <action TYPE=" LOOKUP" TIMELIMIT=" 00:02:00"/>
    <property ID="INF AMI">required</property>
    <property ID="ANT AMI">required</property>
    <property ID="POST AMI">desired</property>
</analysis>
<patientProfile DATE=" 04/08/2000 14:23:33" DATEFORMAT=" M/dd/yyyy h:m:s" ID=" iMedical Systems Inc.
    IMSI200">
    <demographics>
        <property ID="RACE">African American</property>
        <property ID="AGE">56</property>
        <property ID="GENDER">Male</property>
    </demographics>
    <medicalHistory>
        <medHx ID="Hypertention" DATE="06/12/1982" DATEFORMAT="M/dd/yyyy">treated</medHx>
    </medicalHistory>
    <vitalSigns>
        <property ID="SBP">87</property>
        <property ID="DBP">122</property>
        <property ID="TEMPERATURE" UNITS=" DEGREE">98.6</property>
        <property ID="HEARTRATE" UNITS=" BPM">94</property>
    </vitalSigns>
</patientProfile>
``` information to the Analytical Algorithm Development Center for storage, as illustrated by a secure network communication link 211.

It should be readily apparent that such a medical instrument will, through use, acquire specific intelligence that will best serve its particular patient population. This is achieved without prior knowledge of the particulars and specifics of the patient population it will serve. This is ideal for medical instruments that have limited system resources both in terms of local storage and computational facilities. Instead of having to include an analysis capability designed for a broad patient population which only provides limited analysis accuracy or instead of requiring large local storage to facilitate many more analysis capabilities, the described embodiment can be implemented with low-cost medical instruments having very modest storage and computational requirements. In addition, the described embodiment achieves highly adaptive and patient specific analytical capability. One can also use a variety of different consumer devices such as wireless cell phones and networked computers for personal healthcare and medical use.

This XML-based message indicates the analysis type ="Acute Myocardial Infarction" is desired for the diagnosis of possible Acute Myocardial Infarction by the medical instrument—a condition indicating significant decrease in blood supply to the cardiac muscles and thus impending permanent damage to the heart muscles.

Figure 6:
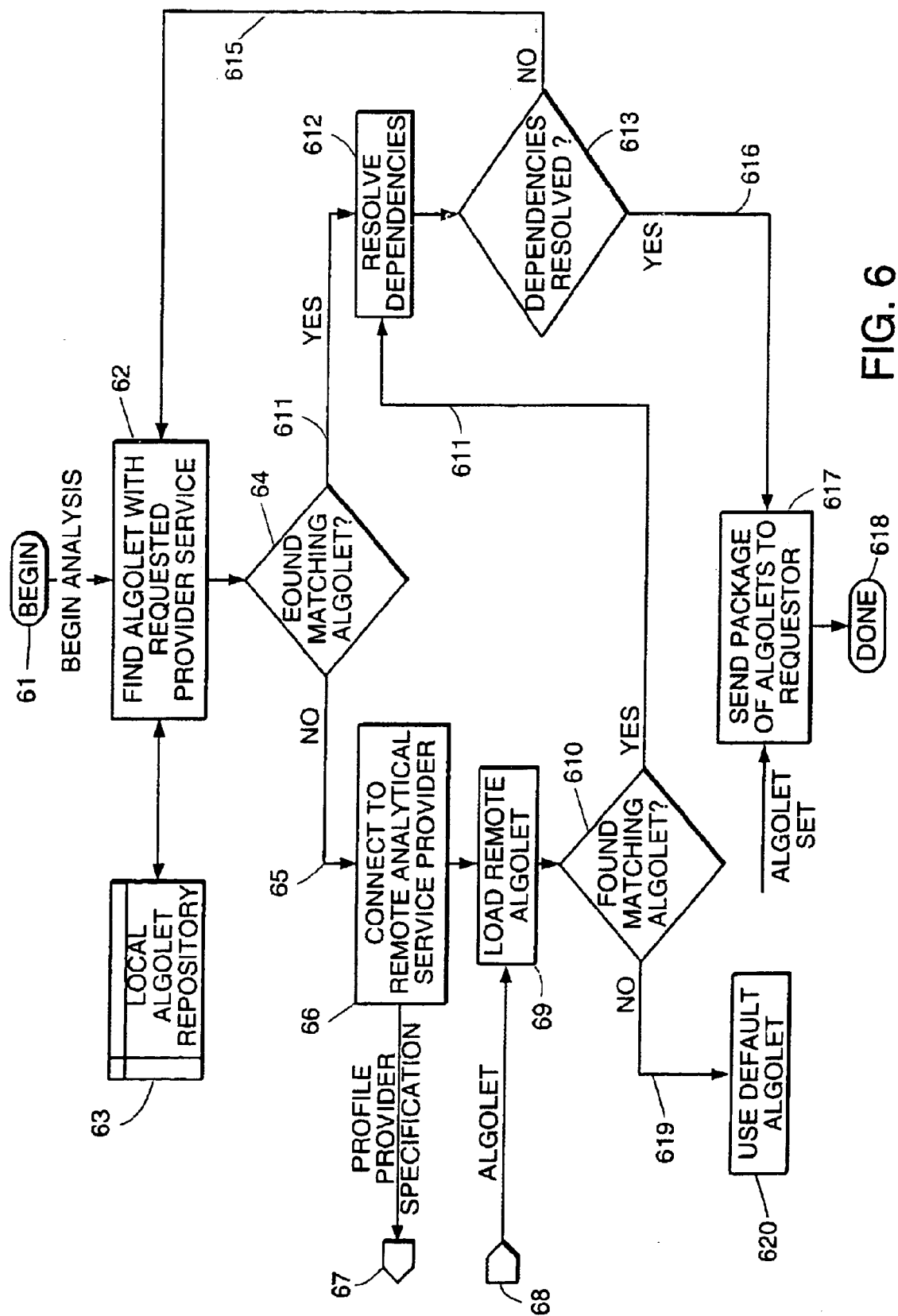
FIG. 6 presents a flowchart of the Algolet lookup method implemented by the networked medical instrument and the Analytical Service Provider.

Server 31 will forward the patient Profile to a processing module 32. Processing module 32, utilizing a search engine 33, first executes a patient profile match to all known Algolets that are capable of providing the desired analysis capabilities. In the described embodiment, search engine 33 includes a database registry of patient characteristics and its associated Algolet Provider Service descriptor. The Algolet Provider Service descriptor is described in detail below (illustrated in FIG. 5), which provides information regarding what analysis capabilities a particular Algolet software component is capable of providing. Once an Algolet is identified by processing module 32 and search engine 33, the Algolet is requested from an Algorithm Lookup Service Provider 34. Algorithm Lookup Service Provider 34, which executes a number of services that will be described in more detail below and are illustrated in FIG. 6, is responsible for acquiring the desired Algolet and its dependent Algolets as requested by processing module 32 from the local repository or from other remote Analytical Service Providers. An Algolet software component in this embodiment is an Object Oriented software component. More specifically, an Algolet is a unit of analysis that may or may not be dependent on other Algolets for support analysis and within a parent-subclass relationship. Therefore resolution of a particular Algolet will require acquisition of all other Algolets utilized by the requested Algolet software component or parent Algolets from which the requested Algolet is derived from.

Lookup Service Provider 34 thus collects and package all Algolets from its local repository 35 and/or from external Analytical Service Provider(s)over a secure communications network. The "resolution" of an analysis request consists of a collection of Algolet software components passed from Algorithm Service Provider 34 to processing module 32. Processing module 32 upon receiving the package of Algolets forwards the package to Network Server 31 which in turn sends the information back to the requesting medical instrument through the same network connection 24.

The Analytical Service Provider is also capable of acquiring new and updated Algolet components as they become available from the Analytical Algorithm Development Center (see FIG. 4) through another secure communication network 37. New and updated Algolets are sent by the Analytical Algorithm Development Center to an Algorithm Update Process 38, which validates and unpacks the updates and installs the various components into Algorithm Search Engine 33 and Algorithm Repository 35.

Analytical Algorithm Development Center

Figure 4:
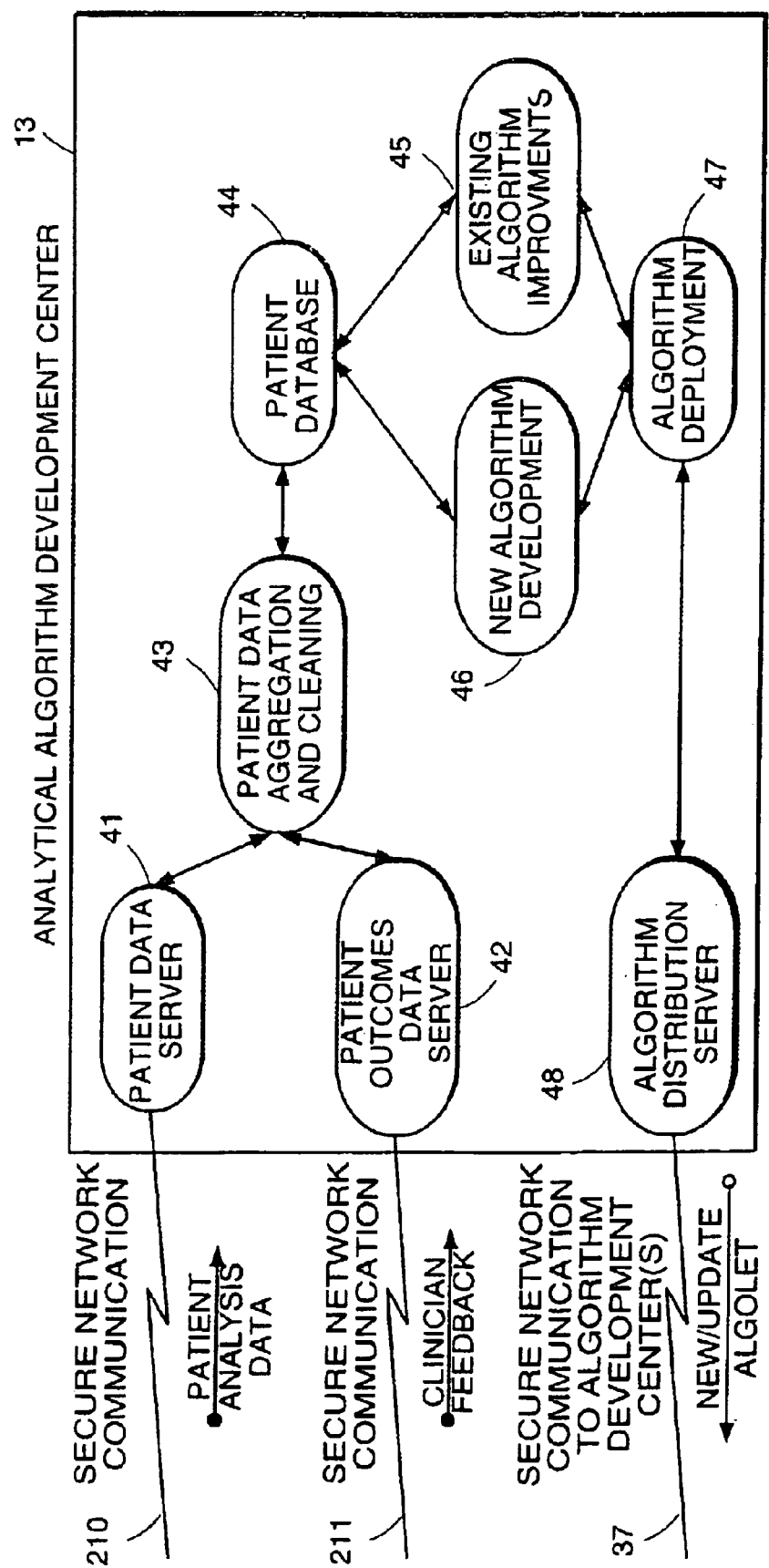
FIG. 4 shows the functionality of the Analytical Algorithm Development Center that is shown in FIG. 1.

FIG. 4 shows the final component of the described embodiment, i.e., the Analytical Algorithm Development Center 13. This is the facility that aggregates and cleans up patient and clinician feedback to form the patient database from which existing algorithms are improved upon and new algorithms developed to provide new analysis capability to address new diseases. It also distributes improved existing and new algorithm software components to one or more participating Analytical Service Provider service centers.

As discussed above, an Algolet is a unit of analysis with a well defined domain. In the described embodiment, the Algolet encompasses the domain of providing analysis of possible Acute Myocardial Infarction (AMI). The analysis of AM1 involves subcomponents such as AM1 in the Anterior region of the heart, AM1 in the Inferior region of the heart, AM1 in the Lateral region of the heart, AM1 in the Posterior region of the heart, and other confounding and supportive analysis. Thus the creation of such analytical components require analysis of patient biological data with the condition from which a mathematical model can be constructed. Such a model may be based on Logistic Regression that utilize a patient's particular demographic characteristics and confirmed diagnosis or the medical condition or disease (e.g. Inferior AMI). For examples of such algorithms, the reader is referred to U.S. Pat. Nos. 4,957,115; 4,998,535; and 5,277,188, all of which are incorporated herein by reference.

A Patient Data Server 41 receives over secure communications network 210 patient analysis data from medical instruments described above. Further, the message is in the form of a L-structured message. Patient Data Server 41 is an HTTP internet server. The patient analysis data received by Patient Data Server 41 is passed to an Aggregation and Clean-Up Process 43 for further processing. Similarly, another HTTP internet server 42 receives clinical feedback and confirmation data through communication network 211 from a clinician (see FIG. 2) or other medical professional or information system involved in the care of the patient. The feedback and confirmation data is forwarded to Aggregation and Clean-Up Process 43 where it is matched to the patient analysis data. Once the patient analysis data and feedback or confirmation data is matched and verified, it is then added to a Patient database 44. Both Aggregation and Clean-Up Process 43 and Patient database 44 utilize an industry standard relational database to process and manage the patient data.

Periodically, an Improvement Process 45 will review and update its Algolets by executing re-generation of the mathematical data model in which the Algolet is based. For example, as the number of patients within the patient population of Male Hispanics between the age of 55 and 75 and have confirmed diagnosis of Inferior AM1 by various clinical means arriving in the Patient Database 44 exceed 10%, Improvement Process 45 automatically recalculates the mathematical coefficients to a Logistic Regression-based algorithm for the Algolet that provides analysis and diagnosis of Inferior AM1 for this particular patient population. The updated Algolet is then distributed through an Algorithm Deployment Process 47 to an Algorithm Distribution Server 48 for distribution. Algorithm Distribution Server 48 is a secure HTTP internet server that connects to and distributes updates to all subscribing Analytical Service Providers through a secure network connection to the Analytical Service Providers.

As an illustration of a further capability, when the number cases for patients within the patient population of Female Pacific Islanders between the age of 35 and 55 having confirmed diagnosis of Posterior AM1 by various clinical means in the Patient Database 44 exceeds a preset minimum threshold, a New Algorithm Development Process 46 will initiate the creation of an Algolet specifically designed for this patient population using Logistic Regression modeling. The newly created Algolet is then distributed through Algorithm Deployment Process 47 to Algorithm Distribution Server 48 for distribution.

Algolet

The described embodiment creates and utilizes a software component called an Algolet that subscribes to the general practices and methodology of Object Oriented Programming design and techniques. FIGS. 5.1 and 5.2 depict an embodiment of the Algolet software component that encapsulates individual patient analysis algorithm for the identification and diagnosis of certain medical conditions and diseases. An Algolet 51 is a software component, referred to as a Class in object oriented terminology, that encapsulates a particular medical analysis capability. As in most Object Oriented Designs (OOD), an Algolet exposes three interfaces, namely, a Provider Interface 52; a Dependencies Interface 53; and a Profile Interface 54. All interfaces provide a set of software Application Programming Interface (API) methods for discovering the various capabilities and characteristics of an Algolet.

Provider Interface 52 provides software API methods to enable a host program to find out what services the Algolet is capable of providing. Example methods include retrieving a XML-based or DOM-based descriptor of what analysis capabilities the Algolet can provide. An example of a XML-based Provider Interface descriptor is given below:

```
<algoletProvider ID="iMedical Systems Inc."VERSION-"1.22.3 A" APPROVAL="FDA 12345">
    <services>
            <service ID="AMI" OUTPUT="Prediction"/>
            <service ID="AMI" OUTPUT="Detection"/>
    </services>
</algoletProviderID>
```

The example Provider Interface descriptor indicates the Algolet is capable of providing both detection and prediction of AMI.

Similarly, Dependencies Interface 53 provides software API methods to enable a host program to find out what other support Algolet is needed by this Algolet in order to fully execute its analysis capabilities as described in Provider Interface 52. An example of an XML-based Dependencies Interface descriptor is given below:

```
<algoletDependencies ID="iMedical Systems Inc." VERSION="1.22.3 A">
    <dependencies>
            <analysis ID="Anterior AMI"/>
            c analysis ID="Inferior AMI"/>
    </dependencies>
</algoletDependencies>
```

The example Dependencies Interface descriptor indicates the Algolet depends on support Algolets that can provide both Anterior AM1 and Inferior AM1 analysis. The dependency descriptor is used by the host program to lookup and collect all Algolets necessary to execute the desired analysis. The lookup service is described in more detail below. Referring to FIG. 5.2, it can be seen that the dependency descriptor is a link to other Algolets through its Provider Interface descriptors as indicated by block 56 and link 57. The illustration in FIG. 5.2 shows that Algolet A (block 56)is dependent on Algolet B and Algolet C, indicated by blocks 58 and 59, respectively. Further, Algolet B is dependent on other Algolets indicated by link 510.

In addition, Profile Interface 54 provides software API methods to enable a host program to find out to what patient population context should this Algolet should be applied. The Profile Interface descriptor describes the patient population characteristics in which this Algolet is appropriate. This descriptor is used to populate Algorithm Search Engine database 33 described above in connection with FIG. 3 for patient Profile matching. An example of an XML-based Profile Interface descriptor is provided below:

```
<algoletProfile ID="iMedical Systems Inc." VERSION=" 1.22.3 A">
    <demographics>
            <property ID="RACE">Caucasian;African American</property>
            <property ID="AGE">45-72</property>
            <property ID="GENDER">Male</property>
    </demographics>
    <medicalHistory>
            <medHx ID="Hypertention">treated</medHx>
            <medHx ID="Diabetes" >treated</medHx>
    </medicalHistory>
    <vitalSigns>
            <property ID="SBP">60-90</property>
            <property ID="DBP">90-130</property>
            <property ID="HEARTRATE" UNITS=" BPM">30-120</property>
    </vitalSigns>
</algoletProfile>
```

The above Profile Interface descriptor indicates the Algolet is appropriate for a patient population of Caucasian or African American race, between the ages of 45–72, male gender, have had a past history of hypertension and or diabetes, systolic blood pressure of 60–90 mmHg, diastolic blood pressure of 90–130 mmHg, and heart rate between 30–120 bpm.

The use of Algolet in its embodiment of Object Oriented Components enables precise and manageable methods and processes for creating new diverse and dynamic medical analysis software components that plug together to form higher levels of analysis capabilities. As interchangeable software components with well defined and exposed descriptors become available (such components can be produced by various sources such as medical research institutions and commercial entities), they will immediately work within the framework of the networked medical instruments and Analytical Service Providers, similar to what was described above.

Analysis Lookup Service

FIG. 6 presents an Analysis Lookup Service flow chart which shows the Analysis Lookup Service and Packaging methodology that exists in the described embodiment of the networked medical instrument and Analytical Service Provider.

When an analysis request is entered (block 61) such as a request for an Algolet to perform detection of AMI, the Service interrogates (block 62) its local repository 63 of Algolets for an Algolet that can provide the desired analysis service. The Service tests for the condition whether a matching Algolet has been found that can provide the requested analysis service (block 64). If no Algolet is found in the local Algolet repository (branch 65), the Service opens a network connection to a remote Analytical Service Provider over the network such as, but not limited to, an Intranet, the Internet, or wireless network (block 66). The desired analysis capability and patient Profile is sent over the network (block 67). Analytical Service Providers responding to the request send matching Algolet packages back over the same network (block 68) for loading (block 69). Control is then passed to the Service which tests whether the requested analysis capability was found (block 610) (i.e., does the message received contain the desired package of Algolets that will satisfy the desired analysis request?). If the appropriate Algolet was not found (branch 619), the Service will retrieve a package of default Algolets (block 620) and send them to the requestor (block 617) for execution. The default Algolets are provided to support conditions where a network is unavailable or the requested specialized or targeted analysis capability has not yet been developed.

In block 64, if a matching Algolet is found in the local repository or in block 610 if it is found by the remote Analytical Service Provider, the Service passes the package of Algolets to a dependency resolution module. The dependency resolution module interrogates the Algolets to determine what supporting Algolets they depend on (block 612). Then, the Service tests whether all dependencies have been collected (block 613). If dependencies still exist, the Service passes each dependent Algolet description back for a further lookup (block 62). However, if it is determined that all dependencies have been resolved, the Service passes the entire package of Algolets out to the requester of the analysis and the process terminates.

The mathematical model mentioned in connection with the above-described embodiment implemented a predictive instrument that predicted cardiac events and/or outcomes. More specifically, the predictive instrument is an ACI- TIPI (Acute Cardiac Ischemia Time-Insensitive Predictive Instrument) which uses a logistic regression-based equation for computing the probability that the patient is experiencing acute cardiac ischemia. The logistic regression equation is of the form:

$$P = 100\left[1 - \frac{1}{1 + e^{b_0 + \Sigma b_i x_i}}\right]$$

where P is the probability of acute cardiac ischemia, $b_0$ is a constant, and the $b_i$'s are coefficients of the variables $x_i$ which are included in the model. The specific explanatory variables and coefficients are described in detail in the patents that have been previously mentioned herein (e.g. U.S. Pat No. 4,957,115).

But the mathematical model or predictive instrument can be designed for diagnosing other medical problems beyond the above-described cardiac related problems. The extension to circumstances that are not cardiac related is straightforward. For example, in the domain of pulmonary medicine, a patient in an intensive care unit could be under observation for potential respiratory failure. The classical approach is to use on-going single function monitors of indicators such as the patient's heart rate, respiratory rate, and perhaps under some circumstances, blood oxygen saturation. As with the cardiac situation, however, any single one of these parameters has limited utility because of its possible contamination by noise and because of its inherent inability to be a good proxy for the wide variety of clinical features and other factors that are really needed to provide an accurate estimate of the probability of the medical outcome in question. On the other hand, the mathematical model described herein (e.g., logistic regression) that takes into account the heart rate, blood pressure, respiratory rate, blood oxygen saturation level, and perhaps other clinical features, will give a far more accurate indication of and prediction of true respiratory failure. The other clinical features include for example the patient's age, symptoms (e.g. shortness of breath), and the patient's past medical history (e.g., history of smoking, history of prior respiratory failure, etc.). In other words, the mathematical model will give a more accurate and usable (e.g. noise-free) estimate of the patient's condition.

A further example in the pulmonary area may be useful. In the case of imminent respiratory failure, a small increase in respiratory rate and heart rate would likely be missed, or might be overwhelmed by noise, or even if detected might be viewed as insignificant. However, if measured in conjunction with other clinical features, including for example a small decrease in oxygen saturation, these observations when included in a logistic regression (or other mathematical model) will be multiplicative, and thus, give a substantial (accurate and specific) increase in the computed probability of respiratory failure. Thus, since the mathematical model takes multiple factors into account, as in the cardiac monitor situation, it will provide an opportunity to early on detect a change in the computed probability value with sufficient fidelity in the real-time setting to support targeted clinical intervention.

In a generalized monitoring system, the monitor is any device for real-time monitoring of one or more clinical features of the patient and the predictive algorithm is for computing a probability of a medical outcome or diagnosis, based in part on those monitored clinical features. The monitoring device could be a single instrument, as it was in the case of the above-described cardiac monitor which used an electrocardiograph, or it could be a constellation of medical instruments, as will be the case in some of the examples systems described below.

The predictive algorithm uses the output of monitoring device in conjunction with other clinical information about the patient that has been entered by a physician through an input device (e.g. keyboard, network connection, database program, etc.) and computes a probability of a particular medical outcome or diagnosis for the patient. In the described embodiments, the probability of the medical diagnosis or medical outcome is computed using a logistic regression equation of the following general form:

$$P = 100\left[1 - \frac{1}{e^z}\right]$$

where P is the probability of a particular medical outcome or diagnosis, and where z has the following general form:

$$z = b_0 + \sum b_i x_i$$

In this equation, $b_0$ is a constant, and the $b_i$'s are coefficients of the explanatory variables $x_i$ which are included in the model. The variables that are used in the model will of course depend upon the particular medical outcome or diagnosis which is being evaluated. Some examples are presented below along with variables that would be included in the model.

Mathematical models other than the logistic regression equation can of course be employed. The invention is not limited to the use of a logistic regression equation to model the probability of a particular medical outcome or diagnosis.

The following are further examples of predictive algorithms for non-cardiac diagnoses or medical outcomes, along with their likely key clinical variables. In the domain of vascular disorders, a predictive algorithm for pulmonary embolus includes as key variables the same variables as listed above, as well as a modification of the symptoms regarding the suddenness of onset, and also ECG variables related to right heart strain (e.g. relating to QRS complex and ST/T wave changes).

In the domain of neurologic disorders, a predictive algorithm for cerebral hemorrhage (i.e., hemorrhagic stroke) includes as key variables the patient's history of medications (e.g. anticoagulants, etc.), prior history of cardiac disorders that predispose to cerebral thrombosis (e.g. atrial fibrillation, valvular disease), and history of trauma to the head, as well as laboratory tests such as prothrombin time and partial thromboplastin time and platelet count, which are all measures of the clotting ability of the blood. They also include blood pressure, with emphasis on pulse pressure (i.e., a difference between the systolic and diastolic pressure).

In the domain of general surgery, a predictive algorithm for intra-abdominal catastrophe (i.e., the need for emergency surgery) includes as key variables the presence of abdominal pain, the patient's physical findings by the physician of so-called peritoneal signs (rigidity of the abdomen, no bowel sounds, etc.), monitor data such as temperature, heart rate, blood pressure, and potentially x-ray findings that reveal bowel gas pattern.

In the domain of infectious diseases, a predictive algorithm for sepsis (i.e., overwhelming infection that would require certain emergency treatments) includes as key variables the patient's level of consciousness, specific complaints, and monitored physiologic measures such as blood pressure (especially low), heart rate (especially high), respiratory rate (especially high), body temperature (especially either unduly high or unduly low), ECG abnormalities (as not showing a contrary cardiac cause for derangements in heart rate, blood pressure, respiratory rate and other findings in the form of an interaction term in the mathematical model) laboratory tests such as white blood count (either unduly high or unduly low), interleukin levels, and other special blood tests typically available on-line from hospital clinical information systems. Also, other ongoing monitoring data relating to blood and other body fluid culture results, such as are typically available on electronic clinical information systems, are further important explanatory variables relating to the source of sepsis.

Each of the above diagnoses to be predicted has consequences in terms of clinical outcomes including, for example, mortality. Other outcomes that can be predicted by a predictive algorithm include mortality due to acute myocardial infarction or congestive heart failure, as well as conditional outcomes such as are obtained from the thrombolytic predictive algorithm (see U.S. Pat. No. 4,998,535). The use of this approach also applies to other non-cardiac conditions for which prediction of medical outcomes can be conditioned on the use of specific therapies.

The examples presented above are meant to be merely illustrative of the many ways in which a predictive algorithm can be used to evaluate a patient's medical condition. It is not intended that the invention be limited to the few examples that were described here. In general, the predictive algorithm is any algorithm which computes on the basis of a set of clinical features a probability of a medical outcome or diagnosis. It is intended that the invention cover the use of such predictive algorithms to evaluate any medical condition that lends itself to such monitoring, regardless of the particular set of clinical features and regardless of the particular medical outcome or diagnosis. By clinical features, it should be understood that we mean any data form that gives direct information about the clinical, i.e., the medical state of patient. Some of the variables used in the above descriptions have focused on circumstances in which clinical features can be directly acquired in electronic form, such as heart rate and respiratory rate acquired by monitors, such as waveforms acquired by an electrocardiograph, such as oxygen saturation measured by a sensor attached to the patient's finger, and such as biochemical laboratory results. However, other clinical features can be obtained in other forms and in other ways as well. For example, as described above in connection with the use of the cardiac predictive algorithm, direct questioning of the patient provides important clinical features, namely, whether or not the patient is having chest pain and whether chest pains are the chief complaint. Analogously, for a predictive algorithm for predicting various respiratory diagnoses or outcomes, a relevant clinical feature would be an indication as to whether the patient has shortness of breath. These symptoms are linked to the relevant underlying medical processes and can, in combination with other clinical variables in the mathematical model, add important information. And in the case of a predictive algorithm for predicting neurologic problems, relevant clinical features include indications as to whether the patient has a headache and/or neurologic symptoms. In addition, some sources of data that are less directly connected to the patient but nevertheless still represent important clinical features. For example, sociodemographic data such as age and gender are obviously important, as was the case for the cardiac predictive algorithm described above. In addition, other relevant clinical feature data is reflected in medical insurance claims, such as the mere performance of certain tests, the fact of hospitalization, the actual diagnostic code (e.g. the ICD9 Code), etc. A clinical feature is any piece of additional information about the patient, which when incorporated into a mathematical model predicts a given medical outcome.

A medical outcome or medical diagnosis, such as might be predicted by a predictive algorithm, is defined in the following way. A medical outcome is the state of a patient defined in medical terms, typically described in the context of a particular constellation of presenting symptoms and clinical features. In practice, the outcome is selected to be clinically meaningful to the care of the patient. Therefore, an important medical outcome for a patient with a heart attack is mortality. For a person with respiratory failure, it is also mortality but it is also long-term respiratory disability, which might be defined, for example, as lack of ability to do activities of daily living due to shortness of breath as well. For a person with neurologic presenting symptoms, an important medical outcome is preservation of normal mental function as well as mortality.

There is overlap between the concept of medical outcomes and medical diagnoses. For example, when a decision has to be made about a patient, before the clinician can evaluate the likely ultimate outcome, the clinician must first consider the specific medical diagnosis or family of diagnoses that the patient has which require attention. Thus, a diagnosis is, in a sense, an intermediate "outcome". For a person coming to the emergency department with chest pain and/or other signs and symptoms, the first question on the clinician's mind is, what is the diagnosis? If the diagnosis, i.e., the ongoing medical/clinical process, is acute cardiac ischemia (i.e., occlusion of a coronary artery), then this requires treatment to prevent its potential downstream outcomes from occurring (e.g., death) and that treatment is very different from what would be used if the diagnosis is costocondritis (inflammation of the joints of the sternum), stomach ulcer, or some other cause of the symptoms.

Moreover, for all the medical conditions alluded to above, detecting through continuous monitoring of the patient changes in the likelihood of such diagnoses can have very important clinical implications for treatment. That is, very different treatments are needed for acute cardiac ischemia as compared to an ulcer, for respiratory failure as compared to a cold, or for a rupture of a cerebral aneurism as compared to a tension headache. Thus, it can be critically important to detect when the probability of a medical outcome changes.

From the above, it should be apparent that the invention described above can be used with a wide variety of patient monitoring and predictive devices beyond those used for cardiac monitoring. Other monitors with which it can be used include, for example, heart rate monitors, respiratory rate monitors, bioanalyzers, blood oximeters, and fetal monitors, just to name a few. Of course, in those other cases, the underlying predictive instrument instead of predicting the likelihood of the occurrence of a cardiac event would predict the occurrence or presence of another medical outcome or diagnosis.

What is claimed is:

1. An apparatus for monitoring the medical condition of a patient, said apparatus comprising:
    a monitoring device which during use monitors one or more clinical features of the patient;
    a predictive instrument arranged to receive output from the monitoring device and programmed to compute a probability of a medical outcome or diagnosis based on the monitored one or more clinical features, said predictive instrument further programmed to compute said probability by executing an algorithm which models said medical outcome or diagnosis; and
    a user interface through which a user enters information characterizing the patient, wherein said predictive instrument is further programmed to request said algorithm from a remote location.

2. The apparatus of claim 1 wherein the monitoring device is an electrocardiograph.

3. The apparatus of claim 2 wherein the algorithm enables the predictive instrument to compute said probability using a regression equation.

4. The apparatus of claim 3 wherein the regression equation is of the form:

$$P = 100\left[1 - \frac{1}{1 + e^{b_0 + \Sigma b_i x_i}}\right]$$

wherein P is the probability of medical outcome or diagnosis, $b_0$ is a constant, the $x_i$'s are explanatory variables, and the $b_i$'s are coefficients of corresponding explanatory variables.

5. The apparatus of claim 4 wherein P is a probability of acute cardiac ischemia.

6. The apparatus of claim 1 wherein said predictive instrument is programmed to request said algorithm from a server at the remote location.

7. The apparatus of claim 6 wherein said apparatus further comprises a communication interface for communicating with the server over a network and wherein the predictive instrument is programmed to send a request for said algorithm through the communication interface.

8. The apparatus of claim 7 wherein the predictive instrument is further programmed to send a patient profile along with the request for said algorithm and to receive said algorithm from the server through communication interface.

9. The apparatus of claim 8 wherein the patient profile characterizes a specific population to which the patient belongs and said algorithm is tailored for use with members of that specific population.

10. The apparatus of claim 7 wherein the predictive instrument is further programmed to specify in the request an analysis type which corresponds to the medical outcome or diagnosis for which the probability will be computed.

11. The apparatus of claim 1 wherein the predictive instrument includes a local repository for storing code which is to be executed by the predictive instrument and wherein the predictive instrument is programmed to request said algorithm from the remote location for storage in the local repository.

12. An apparatus for enabling a remotely located predictive instrument to compute a probability of a medical outcome or diagnosis based on monitored one or more clinical features of a patient, said apparatus comprising:
    a data storage area which stores a plurality of different algorithms, each of which models a corresponding medical outcome or diagnosis; and
    a server which is programmed to respond to a request from a remote device by retrieving a selected one of said plurality of different algorithms from said data storage and forwarding the selected algorithm to the remote device.

13. The apparatus of claim 12 wherein the request contains a patient profile and the server identifies which of the plurality of different algorithms is the selected algorithm based on the received patient profile.

14. The apparatus of claim 13 wherein the request identifies an analysis type and the server is programmed to retrieve an algorithm from the data storage area that corresponds to the identified analysis type.

15. The apparatus of claim 13 wherein each algorithm among said plurality of algorithms is for computing a probability of a corresponding medical outcome or diagnosis based on monitored one or more clinical features of a patient.

16. A method for evaluating a medical condition of a patient, said method comprising:
    electronically requesting from a server at a remote location an algorithm for computing a probability of a medical outcome or diagnosis;
    electronically receiving from the server at the remote location, said algorithm for computing the probability of a medical outcome or diagnosis;
    monitoring one or more clinical features of the patient; and
    using the received algorithm to compute the probability of the medical outcome or diagnosis for the patient and based on the monitored one or more features.

17. The method of claim 16 further comprising receiving input about the patient and wherein requesting involves sending information characterizing a population to which the patient belongs, said characterizing information based on the information received about the patient.

18. The method of claim 17 wherein the received input about the patient includes information from the group consisting of age, race, gender, medical history, and vital signs.

19. The method of claim 16 wherein requesting involves identifying an analysis type and wherein the received algorithm corresponds to the identified anaylsis type.

20. The method of claim 19 wherein the anaylsis type relates to cardiac disorders.

21. The method of claim 19 wherein the anaylsis type relates to a member from the group consisting of cardiac disorders, vascular disorders, neurologic disorders, infectious diseases, and general surgery outcomes.

* * * * *